United States Patent [19]

Yablon et al.

[11] Patent Number: 5,562,604
[45] Date of Patent: Oct. 8, 1996

[54] PORTABLE THERAPEUTIC DEVICE

[75] Inventors: Jeffrey S. Yablon, 1030 Sproul Rd., Bryn Mawr, Pa. 19010; Armand Pascetta, Wilmington, Del.

[73] Assignee: Jeffrey S. Yablon, Bryn Mawr, Pa.

[21] Appl. No.: 398,816

[22] Filed: Mar. 6, 1995

Related U.S. Application Data

[63] Continuation of Ser. No. 61,951, May 12, 1993, abandoned.

[51] Int. Cl.⁶ .................................................. A61F 7/00
[52] U.S. Cl. .................................. 601/148; 607/104
[58] Field of Search .............................. 601/15, 16, 18, 601/148–153; 607/104; 62/3.3, 3.5

[56] References Cited

U.S. PATENT DOCUMENTS

| 1,603,001 | 10/1912 | Carter . | |
|---|---|---|---|
| 2,832,336 | 4/1958 | Davis et al. . | |
| 3,085,405 | 4/1963 | Frantti | 62/3.5 |
| 3,299,927 | 1/1967 | Clarizio . | |
| 4,112,943 | 9/1978 | Adams . | |
| 4,114,620 | 9/1978 | Moore | 607/104 |
| 4,334,519 | 6/1982 | Cieslak | 607/104 |
| 4,338,944 | 7/1982 | Arkans | 607/104 |
| 4,736,088 | 4/1988 | Bart . | |
| 4,747,408 | 5/1988 | Chan-Chih | 607/104 |
| 4,846,176 | 7/1989 | Golden | 607/104 |
| 4,930,317 | 6/1990 | Klein | 62/3.5 |
| 4,962,761 | 10/1990 | Golden | 607/104 |
| 4,996,970 | 5/1991 | Legare . | |
| 5,074,300 | 12/1991 | Murphy . | |
| 5,080,089 | 1/1992 | Mason | 607/104 |
| 5,197,294 | 3/1993 | Galvan | 62/3.5 |
| 5,241,951 | 9/1993 | Mason | 607/104 |
| 5,269,369 | 12/1993 | Faghri | 607/104 |

OTHER PUBLICATIONS

EBI trade literature entitled, "EBI Breaks the Ice" (Jun., 1992).

Primary Examiner—Sam Rimell
Assistant Examiner—David J. Kenealy
Attorney, Agent, or Firm—Duane, Morris & Heckscher

[57] ABSTRACT

Portable therapeutic devices and methods for employing them are provided by this invention. The devices include a flexible containment bag including a fluid chamber containing a fluid medium and a self-contained pumping means disposed within the device for causing the fluid medium to circulate within the fluid chamber to provide a therapeutic effect upon contacting the device with a patient. In preferred embodiments of this invention, integral electromagnetic transducer assemblies are employed to create a pumping action within serpentine fluid channels, and solid state heat pumps are employed to control the temperature of the fluid during therapy. The devices of this invention are ideal for treating lower back pain and post-operative conditions associated with spinal surgery, as well as veterinarian treatments.

21 Claims, 5 Drawing Sheets

PORTABLE THERAPEUTIC DEVICE

This is a continuation application of application Ser. No. 08/061,951, filed May 12, 1993, now abandoned.

FIELD OF THE INVENTION

This invention relates to therapeutic devices employing circulating media for treating patients with a whirlpool-like swirling motion, and more particularly, to portable therapeutic pads which circulate hot or cold fluids in close proximity to a patient for providing relief and therapy without significantly impeding the patient's daily routine.

BACKGROUND OF THE INVENTION

Recent reports indicate that as much as 80% of the adult population in the United States suffers from lower back pain to some degree or another. Typically, these symptoms are relieved with strong, pain-killing medications which must be used continuously and are often associated with adverse side effects. In an effort to minimize the use of medication and avoid these side effects, therapeutic pads have been developed for providing both hot and cold circulation therapy to a patient suffering from lower back pain. Such devices have also been valuable in reducing the post-operative pain and recovery time of patients following surgery. Although this invention is suitable for post-surgical treatments, such as those employed following laminectomy or discectomy procedures, the primary target is for the treatment of lower back pain of musculo-skeletal or mechanical origin.

One prior art device that alleges usefulness in treating the lower back is provided by Adams, U.S. Pat. No. 4,112,943. Adams discloses a flexible bag equipped with a closed circulation system for providing a therapeutic flow of water at the site of lower back pain. The Adams' system contains a rather bulky pump and storage tank which must be carried along side the patient's bed while the patient is immobilized in a prone position.

Another device disclosed in the EBI Trade Literature entitled "EBI Breaks the Ice" for its TEMPTEK T-1000 CCT Cold Therapy Device (June, 1992), provides post surgical treatment to patients recovering from major spinal surgery. Although treatments with this device are reported to reduce the use of narcotics and sedatives when compared with treatments not employing cold therapy, their use requires the patient to be physically located in close proximity to the pump and temperature control unit and tethered thereto by a rather conspicuous connecting hose.

Despite these advances, there appears to be a need for a therapeutic pad which does not overly restrict the comfort and mobility of a patient during its use. There is also a need for a therapeutic pad which provides a controlled circulation of either a hot or cold fluid medium at any preselected body location.

SUMMARY OF THE INVENTION

This invention provides portable therapeutic devices and methods for using such devices in therapeutic treatments. The devices of this invention include a flexible containment bag including a fluid chamber containing a fluid medium. They also include a light-weight, self-contained pumping means disposed within the device for causing the fluid medium to circulate within the fluid chamber to provide a therapeutic effect upon contacting the device with a patient.

The therapeutic devices of this invention eliminate the need for bulky pumping, heating and cooling apparatus which have limited patient mobility in the past, and have rendered them nearly impossible to wear discretely. The pads and treatments of this invention can be completely portable, and can be used without significantly interfering with the patient's mobility or daily schedule. These devices are also light-weight, preferably weighing less than about 5 pounds, and can be battery-powered, so as to enable their users to undergo hot or cold circulation therapy discretely beneath their clothing.

There is a wide variety of treatments contemplated for the devices of this invention. They can be prescribed for increasing circulation to injured areas by providing heat, which is ideal for remedying lower back pain. They can be used in cold therapy for reducing post-operative pain and narcotics requirements in patients who have undergone surgery. They can also be used by paramedics and other emergency care workers to relieve trauma at accident sites or in areas where electric power is not readily available. The devices of this invention, because of their low cost and portability, can also be used in numerous veterinarian applications, including the care and treatment of thoroughbred race horses and livestock.

In more preferred embodiments of this invention, these devices include solid state heat pumps and electromagnetic transducer pumping elements for providing a continuous circulation of a hot or cold fluid medium. Because of their low power consumption and light-weight, these therapeutic devices can be both energy efficient and comfortable to wear.

BRIEF DESCRIPTION OF THE DRAWINGS

The accompanying drawings illustrate preferred embodiments of the invention according to the practical application of the principles thereof, and in which.

DETAILED DESCRIPTION OF THE INVENTION

Figure 1:
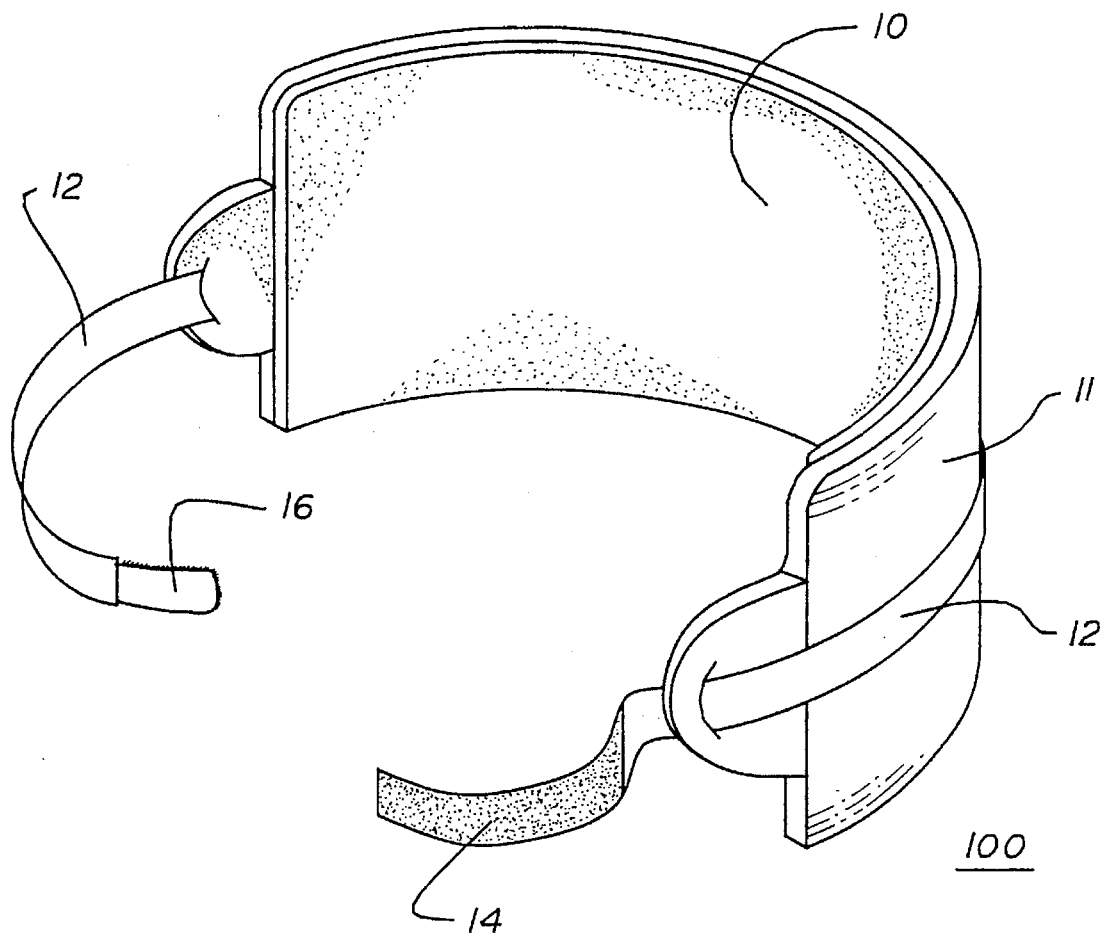
FIG. 1 is a perspective view of a preferred therapeutic pad of this invention just prior to affixing it to a patient.

With reference to the Figures, and particularly to FIG. 1, there is shown a preferred therapeutic pad 100 of this invention. The pad 100 includes a preferred moisture absorbent face 10 disposed to lie on the rectangularly shaped front portion of the pad 100. The moisture absorbent face forms a comfortable surface against the skin of a patient. Preferably, this absorbent face 10 contains a fabric-like covering, such as non-woven polyethylene fabric. One suitable commercial product for this application is 6725 SCOTT (28 gm/yd$^2$), which can be folded around a portion of the pad and is preferably ultrasonically bonded or heat sealed together with the backing layer 11. The non-woven fabric can include an embossed surface, and is preferably water-resistant while also being permeable to sweat or water condensation forming on the skin of the patient. The preferred non-woven fabric of this invention includes a thickness of about 1–5 mils.

The backing layer 11 is preferably constructed of a waterproof thermoplastic film or sheet material such as polyethylene, rubber hydrochloride, vinyl, mylar, or any other suitable thermoplastic. If the therapeutic pad 100 of this invention is designed to be used for heat circulation therapy, certain heat-resistant plastics can be employed for the moisture absorbent face 10 and the backing layer 11. These materials can contain, for example, polyester, vinylester, polyetheretherketone (PEEK), and polyphenylene sulfide (PPS), nylon and fluorocarbons, such as polytetrafluoroethylene (PTFE). Metal foils can also be used, such as those containing aluminum or tin.

The therapeutic pad 100 also preferably includes a mechanism for strapping it to a body portion of a patient. One preferred attachment means is a VELCRO® strap 12 disposed through slots on either transverse end of the pad 100. The preferred VELCRO® attachment means includes a loop connector 14 and hook connector 16 which can be used over and over again, as the need arises. The device is lightweight, weighing less than about 5 pounds, and preferably less than about one pound.

Figure 2:
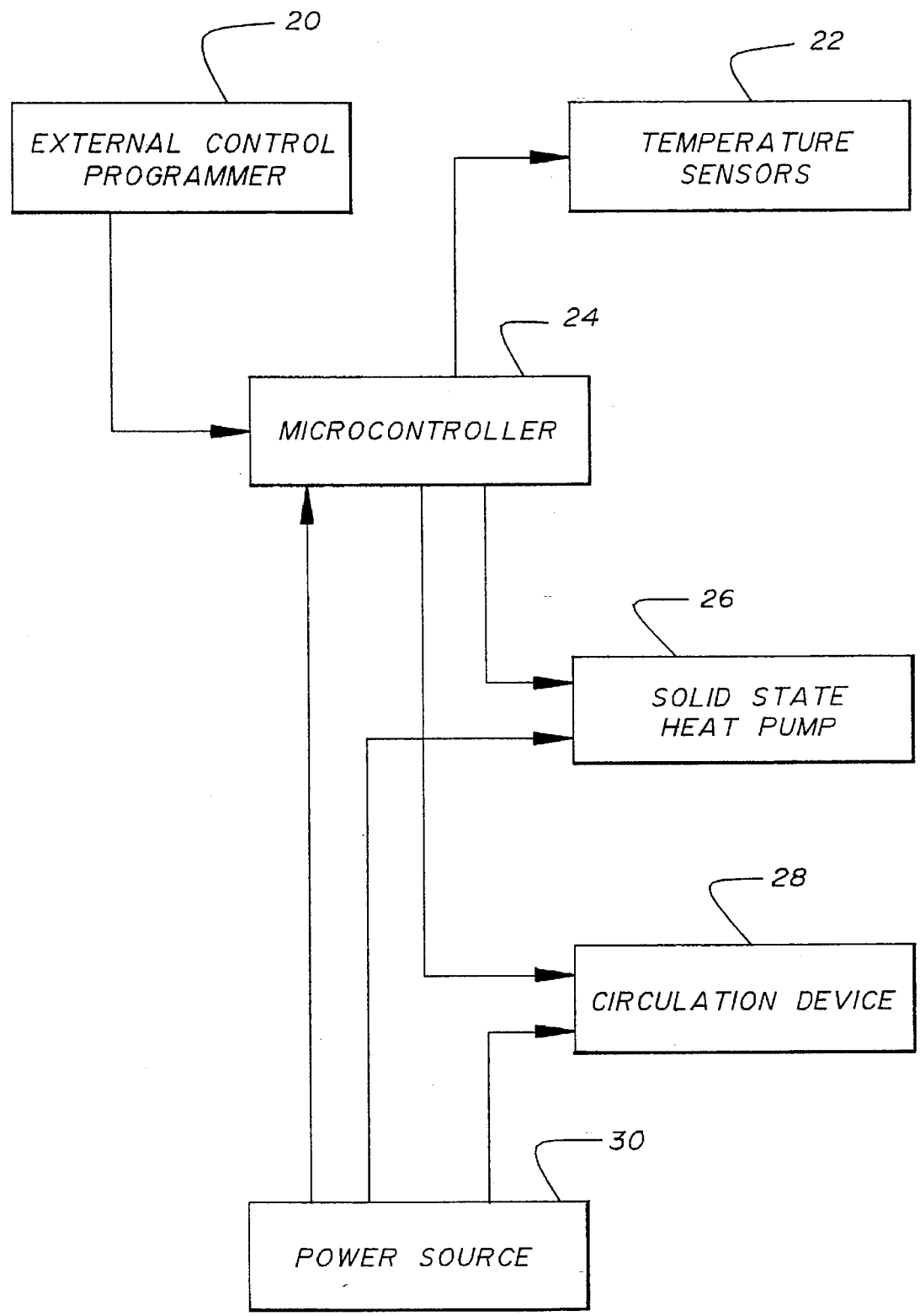
FIG. 2 is a schematic block diagram illustrating the preferred components and operating systems of the therapeutic pad of FIG. 1.

With reference to FIG. 2, the control mechanism of the preferred therapeutic pad 100 of this invention will now be described. The pad 100 preferably includes at its heart, a microcontroller 24 which is used to regulate the temperature sensors 22, solid state heat pump 26, and circulation device 28. The microcontroller 24 can consist of a conventional microprocessor chip of the type normally employed in memory devices and computers. A power supply 30 is also necessary. The device can be internally powered with a rechargeable battery, or externally, with an A.C. power cord. Preferably, the microcontroller 24 also includes means for varying the temperature and pumping parameters, such as an external control programmer 20. In one preferred embodiment, the microcontroller 24 includes a pin array which is exposed on the outside of the pad 100 so that the control functions can be reprogrammed easily.

Figure 3:
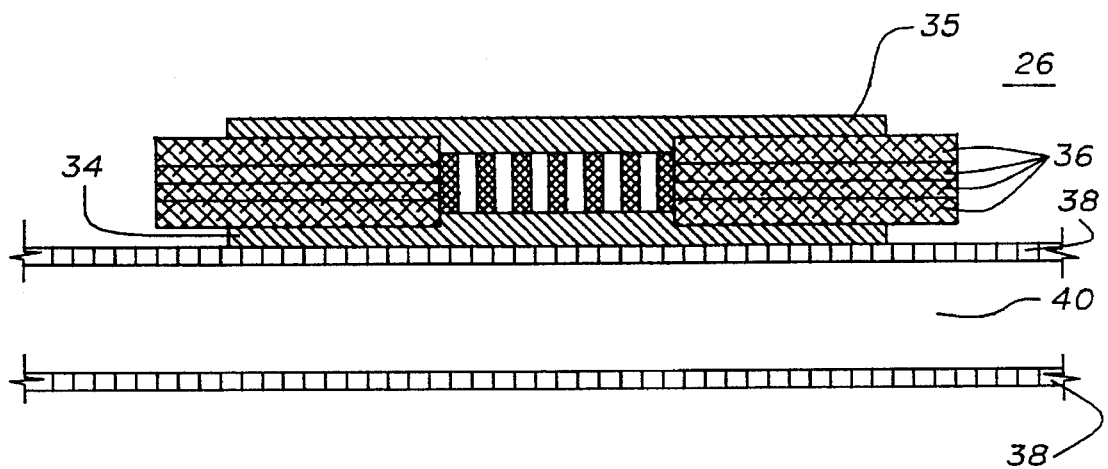
FIG. 3 is a cross-sectional, side view of a preferred solid state heat pump of this invention.

The preferred solid state heat pump 26 and circulation device 28 will now be described with reference to FIGS. 3 and 4. The solid state heat pump 26 of this invention is preferably of the thermoelectrical heating/cooling variety. One such solid state device is available from ITI FerroTec, Chelmsford, Mass. This device is a thermoelectric heating or cooling product, which, being completely solid state, has no moving parts to wear out or cause unnecessary vibration. It therefore can provide both heating or cooling ability to the medium disposed in the fluid channel 40 or 44. This device typically has a size of about 1.7 inches in length by 0.58 inches in width by 0.15 inches in height, to about 1.56 inches in length by 1.56 inches in width by 0.15 inches in height. Numerous other configurations are also possible.

One or more thermoelectric devices may be placed in contact with the fluid medium, or more preferably, in contact with the channel walls 38 of the therapeutic pad 100. They can then be electrically activated so as to produce a temperature gradient between the internal thermal spreader 34 and the external thermal spreader 35. The internal thermal spreader 34 contacts one or more channel walls so as to collect or dissipate heat energy from the fluid medium passing within the channel 40. The external thermal spreader 35 collects or dissipates heat energy to the environment away from the patient. An insulating laminate 36 separates the thermal spreaders 34 and 35 from each other in order to improve thermal efficiency. The device acts as a heat pump by transferring heat energy from one thermal spreader to the other. The transfer is accomplished in a non-mechanical way using known solid state technology. The direction of heat transfer is determined by electrical polarity which may be reversed to selectively reverse the direction of the heat transfer to or from the fluid medium.

Although thermoelectric devices, such as the described solid state heat pump are preferred, this invention contemplates the use of a resealable opening in the containment bag 101 for receiving a preheated or precooled fluid medium, for example, ice water or boiling water. In such circumstances, the heat pump can be eliminated from the device, and the medium can be employed for as long as it takes it to reach room temperature, and then it could be replaced. Moreover, other heating devices can be employed, such as resistive heating elements, or the like, instead of a heat pump.

Figure 4:
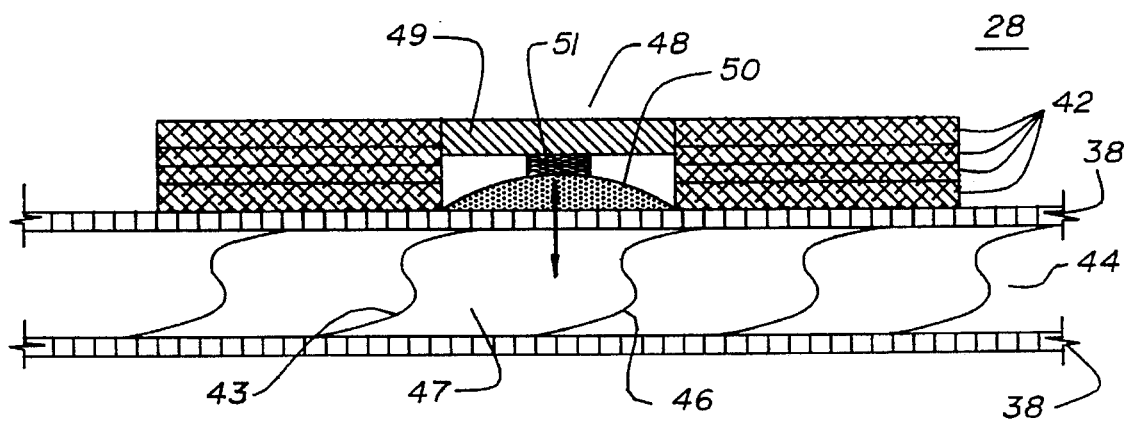
FIG. 4 is a cross-sectional, side view of a preferred electromagnetic transducer pump element of this invention.

With reference to FIG. 4, the preferred circulation device 28 will now be described. This circulation device 28 desirably includes an electromagnetic transducer assembly 48 coupled to the back channel wall 38 of the therapeutic pad 100. The electromagnetic transducer assembly 48 includes a coil and magnetic assembly 51, a diaphragm 50, and a support 49. The support 49 carl have a magnet attached to it which is held at a fixed distance away from the channel wall 38. The coil is preferably attached to the diaphragm 50 so that it may move freely about the magnet. The diaphragm 50 transmits a motion of the coil about the magnet to the channel wall 38 creating a pumping action. The pumping action forces fluid from the pumping chamber 47 and over the downstream flow direction control valve 46. The upstream flow direction control valve 43 is forced closed by reverse pressure acting upon it. The continuous pumping action of the diaphragm 50 effectively forces fluid consecutively through subsequent chambers in a circulating motion—the flow of which is directly proportional to the frequency of the diaphragm pumping action created by the electrical signal driving the coil and magnet assembly 51.

Figure 6:
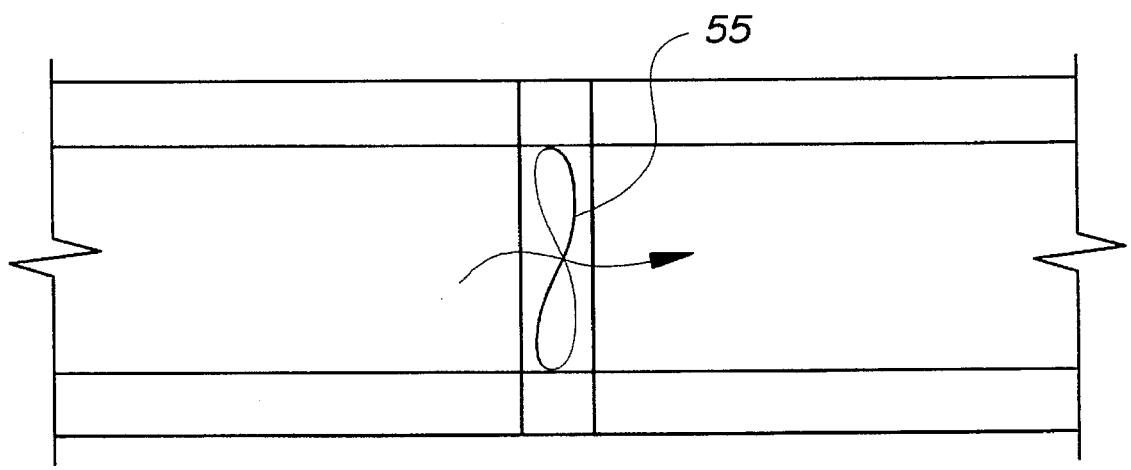
FIG. 6 is a diagrammatic, cross-sectional side view of a preferred impeller pump for moving fluid through the containment bag.

Although the preferred circulation device comprises an electromagnetic transducer pump, a microelectric motor, impeller system 55, shown in FIG. 6, or equivalent device, could be similarly employed to circulate the fluid medium throughout the operative fluid channels 54.

Figure 5:
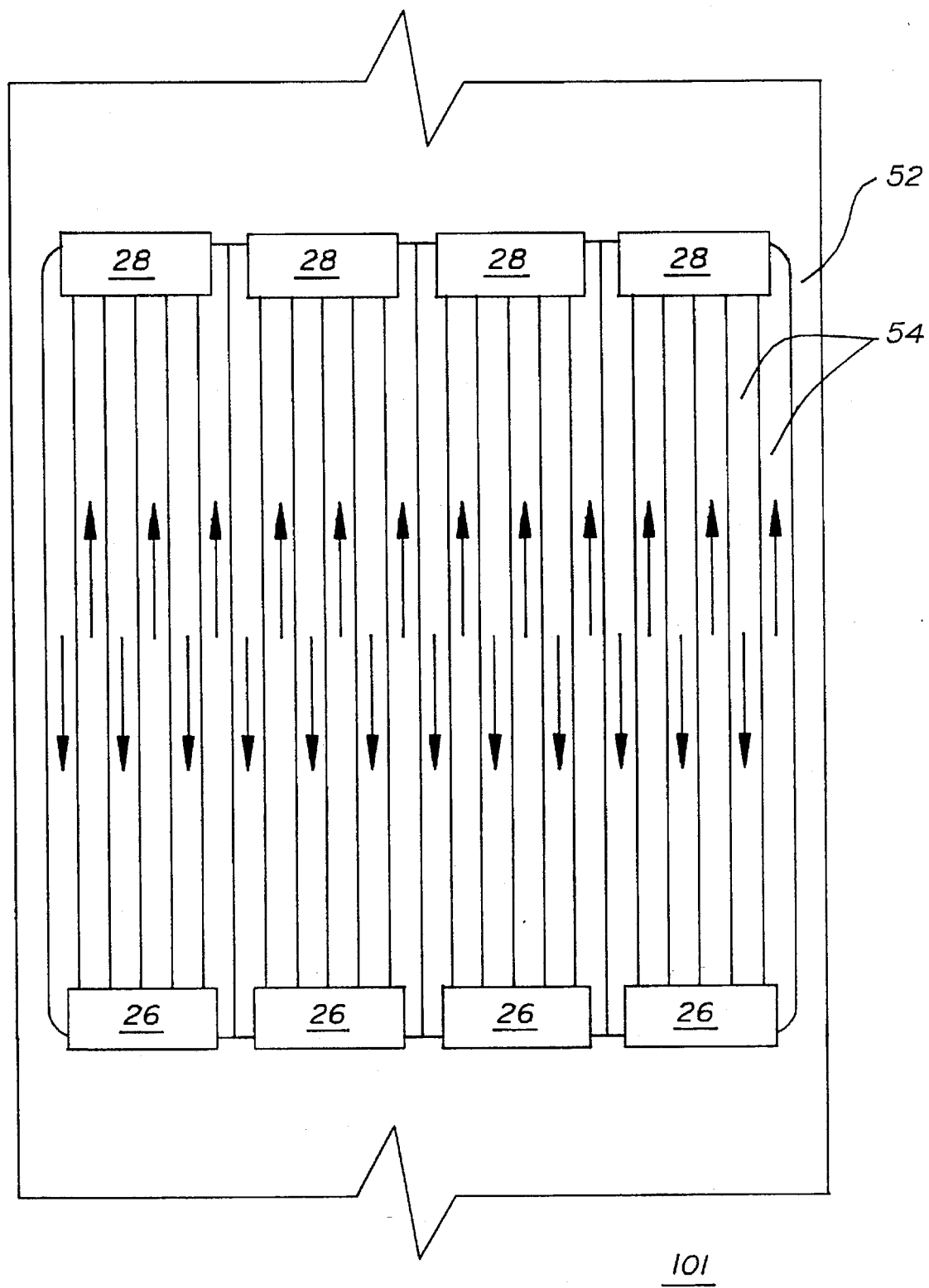
FIG. 5 is a partial, peel-away, top view of the containment bag portion of the preferred therapeutic pad of this invention.

A series of circulation devices 28 and solid state heat pumps 26 of this invention can be disposed along the perimeter of the containment bag 101 as described in FIG. 5. The preferred containment bag 101 includes a perimeter seal 52 disposed around the edge of the containment bag 101 to prevent the leakage of any fluid medium employed in the therapeutic pad 100. Preferably, the solid state heat pumps 26 and circulation devices 28 are alternatively spaced so as to provide uniform heating and pumping of the fluid medium during use. The preferred operative fluid channels 54 can take on any uniform, continuous configuration, such as a serpentine rectangular shape, or a swirling circular shape. Of course, if sufficient turbulence or fluid flow can be derived, for example, by the use of an impeller, the individual channel arrangement can be eliminated entirely, in favor of an open containment area, such as that usually employed in ice packs and the like.

The fluid medium of this invention can contain any liquid or gaseous medium that is sufficient to retain and transfer a therapeutic temperature, either above or below body temperature. Suitable fluid media include anti-freezes, such as methanol, denatured ethanol, glycerol, and ethylene glycol. These anti-freezes can be admixed with water to form a solution or used in their pure state. Anti-freeze formulations should be capable of efficient heat-transfer, anti-boiling, and freeze-depressing characteristics.

From the foregoing, it can be realized that this invention provides therapeutic pads that are both light-weight and self-contained. The pads of this invention are relatively portable, and can be used more discretely and conveniently than recirculation devices that employ large cumbersome pumping mechanisms. Although various embodiments have been illustrated, this was for the purpose of describing, and not limiting the invention. Various modifications, which will become apparent to one skilled in the art, are within the scope of this invention described in the attached claims.

What is claimed is:

1. A portable therapeutic device for treating a patient undergoing hot or cold therapy, comprising:
   a flexible containment bag including a fluid chamber containing a liquid;
   a self-contained source of a therapeutic temperature;
   self-contained microelectric pumping means integrally disposed with said flexible containment bag for causing said liquid to circulate within said fluid chamber; and
   self-contained microcontroller means for controlling a heat transfer between said temperature source and said liquid; said device being substantially compact, weighing less than 5 lbs., and capable of being worn discreetly, without immobilization.

2. The therapeutic device of claim 1, wherein said fluid chamber comprises a plurality of connecting channels.

3. The therapeutic device of claim 1, wherein said liquid contains an antifreeze.

4. The therapeutic device of claim 1, wherein said self-contained pumping means comprises an electromagnetic transducer assembly.

5. The therapeutic device of claim 1 further comprising a reversible solid state heat pump employing a thermal spreader mechanism.

6. The therapeutic device of claim 1 further comprising a moisture absorbing layer on a front portion of said device and a backing layer on the back portion of said device.

7. The therapeutic device of claim 2 further comprising a peripheral seal for containing said plurality of channels, said pumping means comprising a plurality of circulation devices.

8. A portable therapeutic device, comprising:
   a battery; a flexible containment bag means comprising a sealed, closed-loop fluid channel containing a liquid;
   microelectric electromagnetic pumping means integrally disposed with said flexible containment bag means for causing said liquid to circulate through said closed-loop fluid channel;
   a self-contained source of a therapeutic temperature; and
   microprocessor temperature control means integrally disposed with said flexible containment bag for altering a heat transfer between said therapeutic temperature source and said liquid;
   said device being substantially compact, weighing less than five pounds, and capable of being worn by a patient discreetly, without immobilization.

9. The therapeutic device of claim 8, wherein said flexible containment bag comprises a rectangular shape having serpentine connecting channels therein.

10. The therapeutic device of claim 8, wherein said microprocessor temperature control means comprises a reversible solid state heat pump.

11. The therapeutic device of claim 8, wherein said pumping means comprises an impeller.

12. The therapeutic device of claim 8, whereby said microprocessor temperature control means can be adjusted to selectively provide heating or cooling.

13. A portable therapeutic treatment, comprising:
    providing a portable therapeutic device, including a containment bag having a fluid chamber containing a liquid therein; said device further including self-contained microelectric pumping means integrally disposed with said containment bag for causing said liquid to circulate within said fluid chamber;
    a self-contained source of a therapeutic temperature;
    self-contained microcontroller means for controlling a heat transfer between said temperature source and said liquid; said device being substantially compact, weighing less that 5 lbs. and capable of being worn by a patient discreetly, without immobilization; and
    contacting said therapeutic device with a portion of a patient's body while said liquid is circulated within said fluid chamber to provide a therapeutic effect.

14. The treatment of claim 13, wherein said patient is suffering from post-operative pain.

15. The treatment of claim 13, wherein said patient is suffering from a sports injury.

16. The treatment of claim 13, wherein said patient is suffering from lower back pain.

17. The treatment of claim 13, wherein said patient is an animal.

18. The treatment of claim 13, wherein said pumping means comprises an electromagnetic transducer assembly.

19. The therapeutic device of claim 8, wherein said pumping means comprises an electromagnetic transducer assembly.

20. The therapeutic device of claim 8, wherein said therapeutic temperature source comprises a preheated or precooled medium.

21. The therapeutic device of claim 8, wherein said microprocessor temperature control means can vary a pumping parameter of said pumping means to control said heat transfer.

* * * * *